(12) United States Patent
Lorenzo et al.

(10) Patent No.: US 9,220,506 B2
(45) Date of Patent: Dec. 29, 2015

(54) OCCLUSIVE DEVICE WITH STRETCH RESISTANT MEMBER AND ANCHOR FILAMENT

(75) Inventors: Juan Lorenzo, Raynham, MA (US); Robert Slazas, Raynham, MA (US); Peter Forsythe, Raynham, MA (US); Thomas Boden, Raynham, MA (US); Michael Brown, Raynham, MA (US)

(73) Assignee: DEPUY SYNTHES PRODUCTS, INC., Raynham ( * ) Notice: Subject to any disclaimer, the term of this patent is extended or adjusted under 35 U.S.C. 154(b) by 308 days.

(21) Appl. No.: 12/816,694

(22) Filed: Jun. 16, 2010

(65) Prior Publication Data

US 2011/0313443 A1     Dec. 22, 2011

(51) Int. Cl.
*A61M 29/00*     (2006.01)
*A61B 17/12*     (2006.01)
*A61B 17/00*     (2006.01)

(52) U.S. Cl.
CPC ..... *A61B 17/12022* (2013.01); *A61B 17/12113* (2013.01); *A61B 17/12145* (2013.01); *A61B 2017/00526* (2013.01); *A61B 2017/00539* (2013.01); *A61B 2017/12054* (2013.01)

(58) Field of Classification Search
CPC ............ A61F 17/12022; A61F 17/12131; A61F 17/1214; A61F 17/12154; A61F 2017/00526; A61F 2017/00539; A61F 2017/12054
USPC ......... 606/191, 194, 195, 198, 199, 200, 159, 606/108; 623/1.11
See application file for complete search history.

(56) References Cited

U.S. PATENT DOCUMENTS

| | | | |
|---|---|---|---|
| 4,712,553 A | 12/1987 | MacGregor |
| 4,886,067 A | 12/1989 | Palermo |
| 5,045,061 A | 9/1991 | Seifert |
| 5,226,911 A | 7/1993 | Chee |
| 5,263,964 A | 11/1993 | Purdy |
| 5,304,194 A | 4/1994 | Chee |
| 5,549,624 A | 8/1996 | Mirigian |
| 5,582,619 A | 12/1996 | Ken |

(Continued)

FOREIGN PATENT DOCUMENTS

| EP | 1738698 A2 | 1/2007 |
|---|---|---|
| JP | 2007520316 A | 7/2007 |

(Continued)

OTHER PUBLICATIONS

Codman & Shurtleff, Inc.; Trufill DCS Orbit® Detachable Coil System brochure; 2009, Raynham, MA USA. www.codman.com.

*Primary Examiner* — Katrina Stransky

(57) ABSTRACT

A stretch-resistant occlusive device, and method of manufacturing such a device, having a helically wound coil defining a coil lumen extending along the entire axial length of the coil from a proximal end portion to a distal end portion. The device further includes a headpiece having a proximal end, a distal end attached to the proximal end portion of the coil, and a headpiece lumen extending between the proximal and distal ends of the headpiece. An anchor filament extends through the headpiece lumen, has at least one proximal end secured to the proximal end of the headpiece, and has a distal portion defining an eye positioned distal to the distal end of the headpiece. A stretch resistant member is positioned within the coil lumen, has a proximal portion extending through the eye, and has at least one distal end secured to the distal end of the coil.

16 Claims, 3 Drawing Sheets

(56) References Cited

U.S. PATENT DOCUMENTS

| | | |
|---|---|---|
| 5,609,629 A | 3/1997 | Fearnot |
| 5,700,258 A | 12/1997 | Mirigian |
| 5,792,154 A | 8/1998 | Doan |
| 5,853,418 A | 12/1998 | Ken |
| 6,063,100 A | 5/2000 | Diaz |
| 6,171,295 B1 | 1/2001 | Garabedian |
| 6,179,857 B1 | 1/2001 | Diaz |
| 6,183,491 B1 | 2/2001 | Lulo |
| 6,193,728 B1 | 2/2001 | Ken |
| 6,280,457 B1 | 8/2001 | Wallace |
| 6,508,805 B1 | 1/2003 | Garabedian |
| 6,602,261 B2 | 8/2003 | Greene, Jr. |
| 6,692,510 B2 | 2/2004 | West |
| 6,866,660 B2 | 3/2005 | Garabedian |
| 7,070,609 B2 | 7/2006 | West |
| 7,166,122 B2 * | 1/2007 | Aganon et al. ............. 606/200 |
| 7,367,987 B2 | 5/2008 | Balgobin |
| 7,371,251 B2 | 5/2008 | Mitelberg |
| 7,371,252 B2 | 5/2008 | Balgobin |
| 7,485,122 B2 | 2/2009 | Teoh |
| 7,491,214 B2 | 2/2009 | Greene, Jr. |
| 7,572,246 B2 | 8/2009 | Wilson |
| 7,608,058 B2 | 10/2009 | Wilson |
| 7,608,089 B2 | 10/2009 | Wallace |
| 7,651,513 B2 | 1/2010 | Teoh |
| 7,658,750 B2 | 2/2010 | Li |
| 2002/0002382 A1 | 1/2002 | Wallace |
| 2002/0049467 A1 | 4/2002 | Gilson |
| 2002/0128671 A1 | 9/2002 | Wallace |
| 2004/0002731 A1 | 1/2004 | Aganon |
| 2004/0006362 A1 | 1/2004 | Schaefer |
| 2004/0034363 A1 | 2/2004 | Wilson |
| 2004/0127934 A1 | 7/2004 | Gilson |
| 2004/0199175 A1 | 10/2004 | Jaeger |
| 2005/0043755 A1 | 2/2005 | Wilson |
| 2005/0192621 A1 | 9/2005 | Wallace |
| 2006/0052815 A1 | 3/2006 | Fitz |
| 2006/0135986 A1 * | 6/2006 | Wallace et al. ............. 606/200 |
| 2006/0200192 A1 | 9/2006 | Fitz |
| 2006/0206143 A1 | 9/2006 | West |
| 2006/0217758 A1 | 9/2006 | Ogawa |
| 2006/0241685 A1 * | 10/2006 | Wilson et al. ............. 606/200 |
| 2006/0276824 A1 | 12/2006 | Mitelberg |
| 2006/0276825 A1 | 12/2006 | Mitelberg |
| 2006/0276826 A1 | 12/2006 | Mitelberg |
| 2006/0276827 A1 | 12/2006 | Mitelberg |
| 2006/0276828 A1 | 12/2006 | Balgobin |
| 2006/0276829 A1 | 12/2006 | Balgobin |
| 2006/0276830 A1 | 12/2006 | Balgobin |
| 2006/0276832 A1 | 12/2006 | Balgobin |
| 2006/0276833 A1 | 12/2006 | Balgobin |
| 2006/0276834 A1 | 12/2006 | Balgobin |
| 2007/0005096 A1 | 1/2007 | Gilson |
| 2007/0010850 A1 | 1/2007 | Balgobin |
| 2007/0233168 A1 | 10/2007 | Davis |
| 2007/0239193 A1 | 10/2007 | Simon |
| 2008/0046092 A1 | 2/2008 | Davis |
| 2008/0046093 A1 * | 2/2008 | Davis et al. ............. 623/23.72 |
| 2008/0086163 A1 | 4/2008 | Jones |
| 2008/0086217 A1 | 4/2008 | Jones |
| 2008/0306503 A1 * | 12/2008 | Que et al. ............. 606/191 |
| 2009/0062812 A1 | 3/2009 | Fitz |
| 2009/0232869 A1 | 9/2009 | Greene, Jr. |
| 2009/0292303 A1 | 11/2009 | Wilson |
| 2010/0004675 A1 | 1/2010 | Wilson |

FOREIGN PATENT DOCUMENTS

| | | |
|---|---|---|
| JP | 2008049159 A | 3/2008 |
| WO | WO 03096910 A1 | 11/2003 |

* cited by examiner

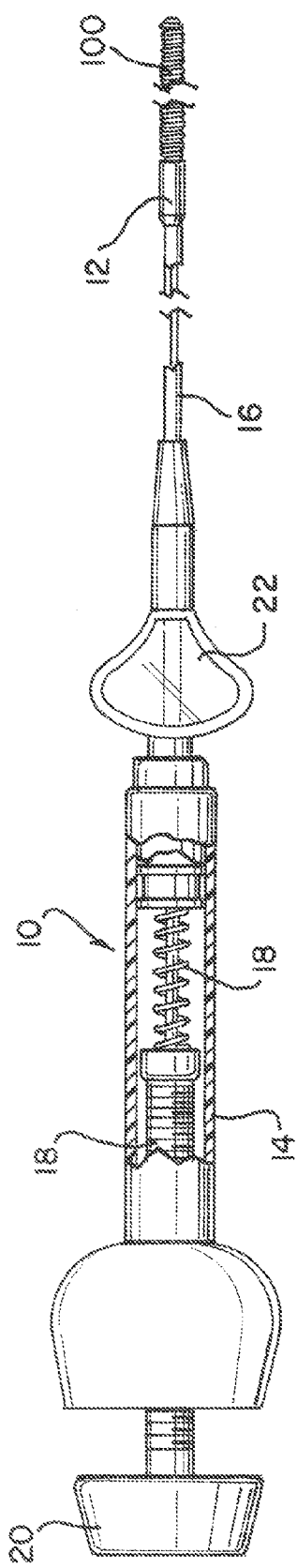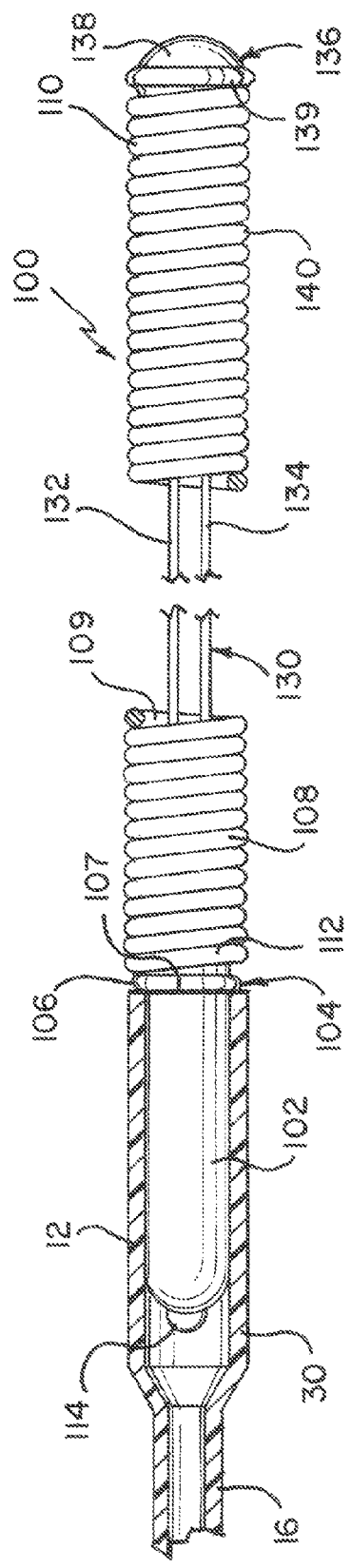

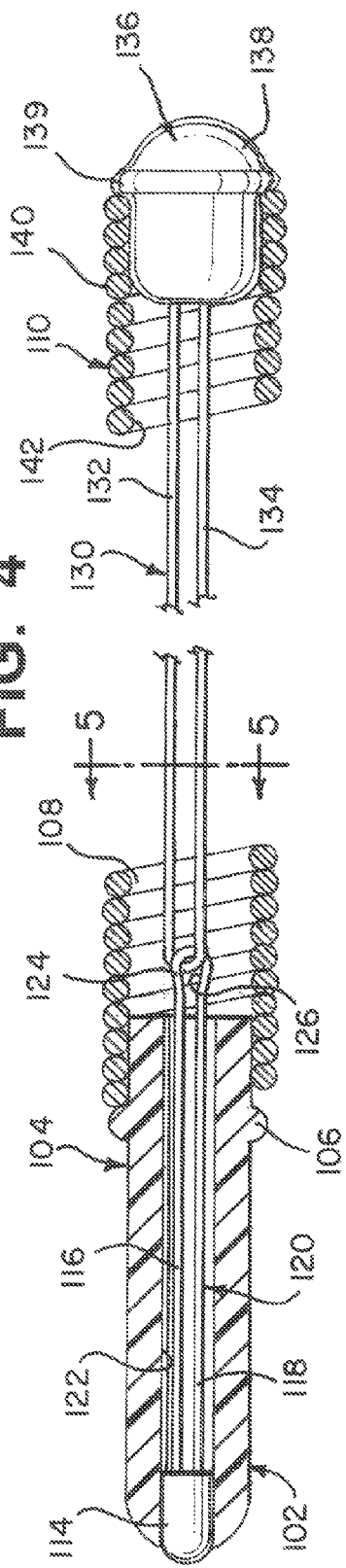
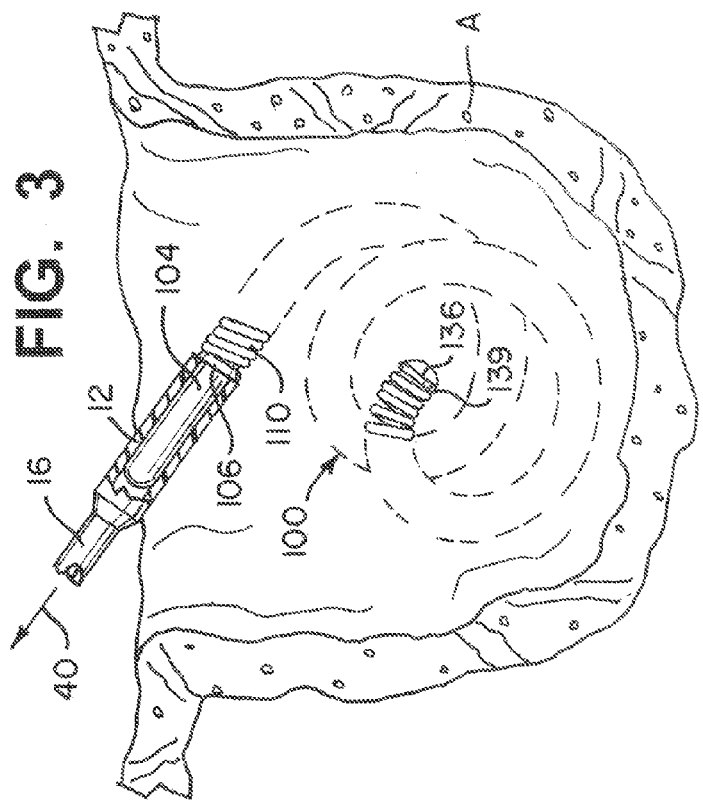
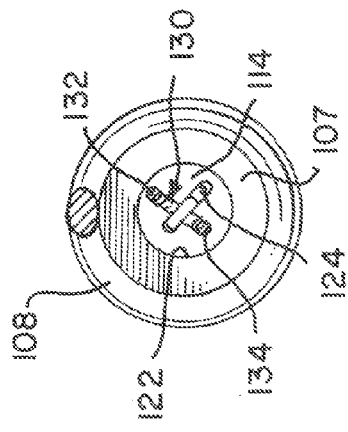

OCCLUSIVE DEVICE WITH STRETCH RESISTANT MEMBER AND ANCHOR FILAMENT

BACKGROUND OF THE INVENTION

1. Field of the Invention

The invention relates to implants within body vessels and more particularly to occlusive devices including embolic coils having stretch resistance.

2. Description of the Related Art

Vascular disorders and defects such as aneurysms and other arterio-venous malformations are especially difficult to treat when located near critical tissues or where ready access to a malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

Alternative treatments include vascular occlusion devices such as embolic coils deployed using catheter delivery systems. In a currently preferred procedure to treat a cranial aneurysm, the distal end of an embolic coil delivery catheter is inserted into non-cranial vasculature of a patient, typically through a femoral artery in the groin, and guided to a predetermined delivery site within the cranium. A number of delivery techniques for vaso-occlusive devices, including use of fluid pressure to release an embolic coil once it is properly positioned, are described by Diaz et al. in U.S. Pat. Nos. 6,063,100 and 6,179,857, for example.

Multiple embolic coils of various lengths, commonly 1 to 30 centimeters, and preselected stiffness often are packed sequentially within a cranial aneurysm to limit blood flow therein and to encourage embolism formation. Typically, physicians first utilize stiffer coils to establish a framework within the aneurysm and then select more flexible coils to fill spaces within the framework. Ideally, each coil conforms both to the aneurysm and to previously implanted coils. Each successive coil is selected individually based on factors including stiffness, length, and preformed shape which the coil will tend to assume after delivery.

During implantation, the physician manipulates each embolic coil until it is in a satisfactory position, as seen by an imaging technique such as fluoroscopic visualization, before detaching the coil from the delivery system. It is highly desired for both ends of each coil to remain positioned within the aneurysm after delivery, because a length of coil protruding into the main lumen of the blood vessel invites undesired clotting external to the aneurysm. After each successive coil is detached, the next coil is at an increasing risk of becoming entangled in the growing mass of coils, thereby restricting the depth of insertion for that coil into the aneurysm.

Difficulties may arise due to stretching of the embolic coils during repositioning or attempted retrieval of the coils, especially if the coil becomes entangled and complete insertion of the coil into the aneurysm is not accomplished. If pulling forces applied to a coil exceed its elastic limit, the coil will not return to its original shape. A stretched coil exhibits diminished pushability or retractability, and becomes more difficult to manipulate into an optimal position or to be removed. Moreover, a stretched coil occupies less volume than an unstretched coil, which increases the number of coils needed to sufficiently pack the aneurysm to encourage formation of a robust embolus positioned wholly within the aneurysm.

There have been a number of attempts to address stretch-related problems in embolic coils. Several stretch-resistant devices are disclosed in U.S. Pat. No. 5,853,418 to Ken et al., having a primary coil and an elongated stretch-resisting member fixedly attached to the primary coil in at least two locations. While Ken et al. mention possible hydraulic delivery of their coils through a lumen of a catheter, they teach that it is desirable to controllably release each coil using a severable or mechanical joint such as an electrolytically detachable joint. Such joints are not compatible with certain delivery systems, and some physicians prefer not to use electrical currents to detach embolic coils from a delivery catheter.

Another embolic device, described in U.S. Pat. No. 6,183,491 by Lulo, has a support wire attached at one end to a proximal end of the coil and attached at its other end to an attachment point located in an intermediate portion of the coil. The embolic device has a closed proximal end and is suitable for hydraulic release from a delivery system after the device is properly positioned. However, only the proximal portion of the coil resists stretching; any length of coil distal to the intermediate attachment point is unprotected from excessive elongation forces.

It is therefore desirable to have an improved stretch-resistant occlusive device which retains flexibility and conformability during insertion into a vascular malformation yet resists stretching along its entire length when pulling forces are applied to it. It is also desirable to have such a device which is compatible with hydraulic deployment systems.

SUMMARY OF THE INVENTION

An object of the present invention is to maintain high flexibility and conformability in an occlusive device while providing resistance to stretching.

Another object of the present invention is to provide stretch resistance without impairing the ability of an embolic coil to assume a pre-formed shape after delivery to an arterio-venous malformation.

It is yet another object of the invention to enable delivery of novel stretch-resistant embolic coils using certain existing microcatheter systems having very flexible distal ends.

A still further object of the invention is to enable controllable and consistent manufacture of small-diameter, highly flexible embolic coils having novel additional components to handle elongation forces while maintaining compatibility of the coils with selected microcatheter delivery systems.

This invention results from the realization that stretch resistance can be added to helically wound occlusive devices such as embolic coils by utilizing a novel proximal headpiece portion defining a headpiece lumen, and a novel proximal anchor filament passed distally through the headpiece lumen and joined with a flexible distal stretch resistant member to create a stretch-resistant assembly. The stretch-resistant assembly extends along the entire axial interior of the helically wound coil to minimize undue coil elongation without impairing coil flexibility and conformability during and after implantation.

This invention features an occlusive device having a helically wound coil defining a coil lumen extending along the entire axial length of the coil from a proximal end portion to a distal end portion. The device further includes a headpiece having a proximal end, having a distal end attached to the proximal end portion of the coil, and defining a headpiece lumen extending between the proximal and distal ends of the headpiece. An anchor filament extends through the headpiece lumen, has at least one proximal end secured to the proximal end of the headpiece, and has a distal portion defining an eye positioned distal to the distal end of the headpiece. A stretch resistant member is positioned within the coil lumen, has a proximal portion extending through the eye and has at least one distal end secured to the distal end of the coil.

In some embodiments, the proximal end of the anchor filament is secured to the proximal end of the headpiece with both structural and hydraulic integrity. In other embodiments, the anchor filament has two proximal ends secured to the proximal end of the headpiece with structural and hydraulic integrity, and has a distal bight portion defining the eye. The stretch resistant member preferably has two distal ends secured to the distal end of the coil. In some embodiments, the anchor filament and the stretch resistant member are composed of different materials, for example, the anchor filament includes metallic material and the stretch resistant member includes a loop of polymeric material.

In another embodiment, the helically wound coil is substantially cylindrical and defines the coil lumen to have a lumen diameter at its proximal end. The headpiece is substantially cylindrical with a mean distal diameter and a mean proximal diameter, and further includes at least one stop element, such as a ring member, positioned between the proximal and distal mean diameters and projecting radially outwardly beyond both mean diameters. Preferably, the ring member has a stop diameter that is greater than the mean diameters of the headpiece and is greater than the proximal coil lumen diameter.

This invention also features a method of manufacturing an occlusive device such as an embolic coil by attaching a distal end of a headpiece to a proximal end portion of a helically wound coil defining a coil lumen extending along the entire axial length of the coil and having a coil distal end portion. The headpiece also has a proximal end and defines a headpiece lumen extending between the proximal and distal ends of the headpiece. Next, a distal portion of an anchor filament, defining an eye, is advanced distally through the headpiece lumen and through the coil lumen to expose the eye beyond the coil distal end portion. A stretch resistant member is passed through the eye to join the member with the filament to create a stretch-resistant assembly extending through the coil lumen and the headpiece lumen, and the anchor filament is retracted to bring the eye in proximity to the distal end of the headpiece. The anchor filament is secured to the proximal end of the headpiece so that the eye is positioned distal to the distal end of the headpiece, and the stretch resistant member is secured to the distal end of the coil, with an atraumatic distal surface, so that proximal and distal ends of the stretch-resistant assembly are secured to resist pulling forces which may be applied to the helically wound coil during implantation in a patient.

In some embodiments, the method includes forming the anchor filament to have two proximal ends secured as a proximal bead to the proximal end of the headpiece with structural and hydraulic integrity, with a distal bight portion defining the eye, and forming the stretch resistant member into a loop passing through the eye with two distal ends secured to the distal end of the coil by a distal bead having the atraumatic distal surface. The anchor filament and the stretch resistant member are composed of different materials, preferably the anchor filament being selected to include metallic material and the stretch resistant member being selected to include a loop of polymeric material. The helically wound coil is selected to be substantially cylindrical and defines the coil lumen to have a lumen diameter at its proximal end, and the headpiece is selected to be substantially cylindrical with a mean distal diameter and a mean proximal diameter, and to further include at least one stop element positioned between the proximal and distal mean diameters and projecting radially outwardly beyond both mean diameters.

BRIEF DESCRIPTION OF THE DRAWINGS

In what follows, preferred embodiments of the invention are explained in more detail with reference to the drawings, in which:

FIG. 1 is a partially sectioned top view of a vascular occlusive coil hydraulic deployment system with an improved occlusive device according to the present invention;

FIG. 2 is an enlarged partially sectioned view showing the distal gripper portion of the deployment system releasably holding the headpiece of the occlusive device;

FIG. 3 is a schematic rendering of the occlusive device of FIG. 2 being delivered into an aneurysm of a patient;

FIG. 4 is a side sectioned view of the occlusive device shown in FIG. 2;

FIG. 5 is a cross-sectional view of FIG. 4;

DETAILED DESCRIPTION OF THE PRESENTLY PREFERRED EMBODIMENTS

Figure 6:
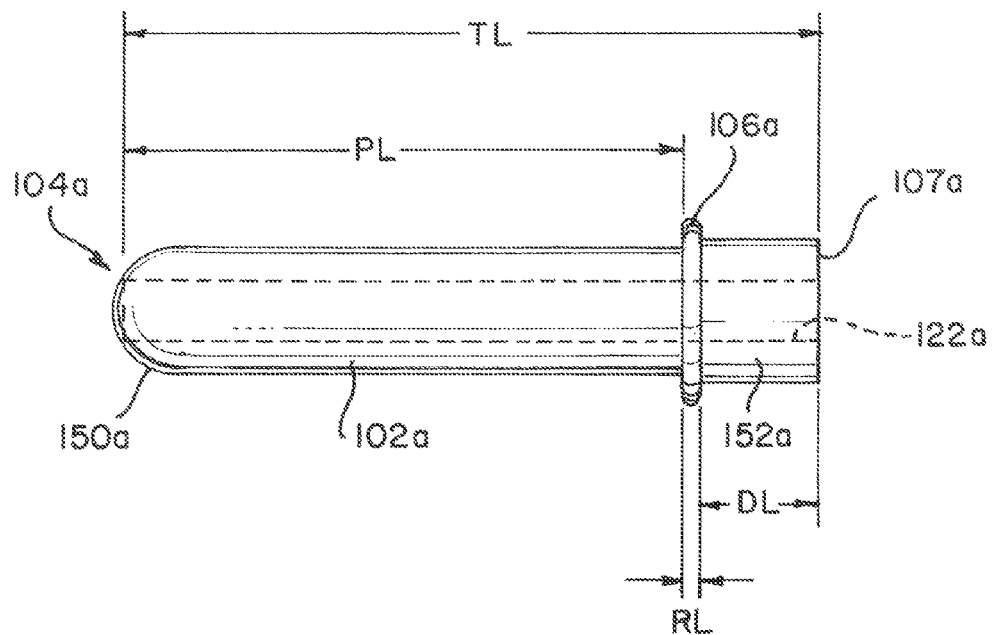
FIG. 6 is a side view of another headpiece according to the present invention.

Stretch resistance is provided to helically wound occlusive devices such as embolic coils according to the present invention by utilizing a novel proximal headpiece portion defining a headpiece lumen, and a novel proximal anchor filament passed distally through the headpiece lumen and joined with a flexible distal stretch resistant member. Together, the anchor filament and the stretch resistant member may be referred to as a stretch-resistant assembly which extends along the entire axial interior of the helically wound coil to minimize undue coil elongation without impairing coil flexibility and conformability during and after implantation.

FIG. 1 illustrates an occlusive device 100 according to the present invention releasably held at the distal end 12 of a vascular occlusive coil hydraulic deployment system 10. System 10 includes a hydraulic injector or syringe 14 coupled to the proximal end of a catheter 16. Syringe 14 includes a threaded piston 18 which is controlled by a handle 20 to infuse fluid under high pressure into the interior of catheter 16 when it is appropriate to hydraulically release device 100. Winged hub 22 aids in the insertion of the catheter 104 into the vasculature of a patient.

The occlusive device 100, which is an embolic coil in this construction, and the distal end 12 of catheter 16 are shown in more detail in FIG. 2. Distal end 12 includes a gripper portion 30, shown in sectional view, tightly holding proximal portion 102 of headpiece 104. Enlarged ring 106 of headpiece 104 limits insertion of headpiece 104 into gripper portion 30, serving as a distal stop as device 100 is releasably connected to catheter 16 prior to insertion into a patient. Another surface of ring 106 serves as a proximal stop during insertion of headpiece distal end 107 into proximal portion 108 of helically wound coil 110, defining proximal coil lumen 109, as described in more detail below. In this construction, proximal-most coil turn 112 of coil 110 abuts ring 106.

As shown in FIG. 3, distal end 12 of catheter 16 may be retracted in the direction of arrow 40 to reposition embolic coil 100 relative to aneurysm A. When the physician is satisfied with the placement of the entire length of device 100 including its proximal and distal ends, hydraulic pressure is applied, typically at least 150 psi to about 700 psi, more typically between 500 psi to 650 psi, through catheter 16 to forcibly release headpiece 104 and thus relinquish control over device 100. After the headpiece 104 is released, catheter 16 of the delivery system is withdrawn, such as in the direction of arrow 40.

Referring particularly to FIGS. 2 and 4, hydraulic integrity of headpiece 104, which would otherwise be compromised by headpiece lumen 122, necessary to withstand high fluid release pressures is provided in this construction by proximal bead 114 which also structurally secures proximal legs 116 and 118 of anchor filament 120 extending distally through headpiece lumen 122. A distal portion of anchor filament 120 forms bight 124 which defines eye 126. Legs 116 and 118 in this construction are portions of a continuous wire which is folded to form bight 124; in other constructions, anchor filament 120 is a unitary element defining eye 126 similar to a sewing needle having an eye through which thread is passed.

A stretch resistant member 130 passes through eye 126 and extends distally as a loop with two legs 132 and 134 that terminate in distal bead 136 having atraumatic distal surface 138. A cross-sectional view through proximal coil portion 108 showing headpiece distal end 107, and anchor bight 124 distal to headpiece lumen 122, as seen within coil lumen 109 is illustrated in FIG. 5, as if stretch member legs 132 and 134 and coil 110 are extending out of the drawing toward the viewer. Distal bead 136, FIG. 4, is secured to distal portion 140 of coil 110 at least by having an enlarged head 139 which is greater in diameter than distal coil lumen 142 of distal coil portion 140.

A procedure for manufacturing stretch-resistant occlusive devices such as embolic coils according to one embodiment of the present invention includes some or all of the following steps. A distal end of a headpiece is attached to a proximal end portion of a helically wound coil defining a coil lumen extending along the entire axial length of the coil and having a coil distal end portion. The headpiece also has a proximal end and defines a headpiece lumen extending between the proximal and distal ends of the headpiece. Next, a distal portion of an anchor filament, defining an eye, is advanced distally through the headpiece lumen and through the coil lumen to expose the eye beyond the coil distal end portion. A stretch resistant member is passed through the eye to join the member with the filament to create a stretch-resistant assembly extending through the coil lumen and the headpiece lumen, and the anchor filament is retracted to bring the eye in proximity to the distal end of the headpiece. The anchor filament is secured to the proximal end of the headpiece so that the eye is positioned distal to the distal end of the headpiece, and the stretch resistant member is secured to the distal end of the coil, with an atraumatic distal surface, so that proximal and distal ends of the stretch-resistant assembly are secured to resist pulling forces which may be applied to the helically wound coil during implantation in a patient.

Helically wound coil stock is formed initially by winding a platinum-tungsten alloy wire about an elongated, non-curved mandrel to generate tight uniform helical turns defining a central lumen occupied by the mandrel. It is currently preferred for tungsten to comprise approximately six percent to ten percent of the alloy wire. Stiffer framing coils are formed by using round wire having a diameter of approximately 0.003 inch. More flexible fill coils utilize round alloy wire having a diameter of approximately 0.002 inch while even softer coil wire is approximately 0.0015 inch in diameter. The softer wire typically is wound over a slightly larger mandrel to generate a slightly larger wound coil diameter defining a correspondingly larger coil lumen. In other constructions, different alloys or material, or a tapered mandrel geometry, could be utilized to alter flexibility of the resulting helically wound coil.

After the mandrel is removed, the initial linear coil stock is cut to desired lengths, typically 1.5 cm to 30 cm, and each length may be thermally "set" into a desired overall curved, non-linear configuration that it will tend to assume after implantation. Configurations having a curved longitudinal axis include a helical or spiral shape and even more complex shapes. Various detachable embolic coils, each having a solid proximal headpiece that is releasably held by a polymeric distal gripper portion of a hydraulic delivery tube during cranial implantation, are currently commercially available as part of the TRUFILL® DCS ORBIT® Detachable Coil System from Codman & Shurtleff, Inc. of Raynham, Mass.

Figure 7:
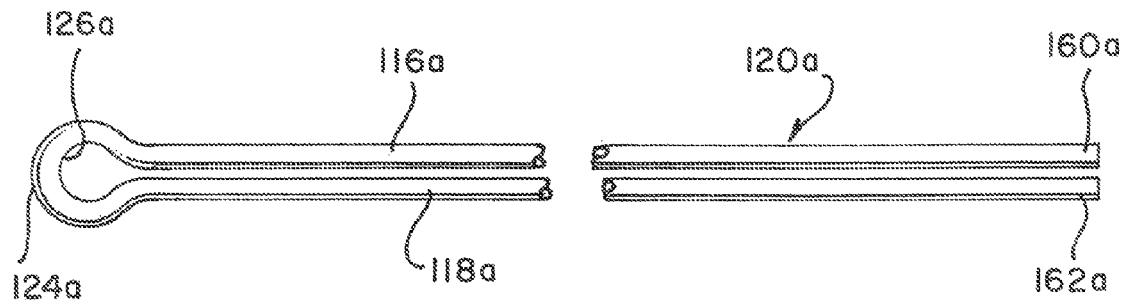
FIG. 7 is a side view of an anchor filament according to the present invention.

Novel headpieces according to the present invention define a headpiece lumen through which novel anchor filament is passed after the headpiece is attached to the proximal end of the external coil by a solder joint, welding or other secure bond. Examples of compatible headpiece and anchor filament components prior to assemblage are shown in FIGS. 6 and 7, respectively, but are not drawn to scale. Headpiece 104a, FIG. 6, has a total length TL of 0.042 inch, a proximal portion length PL of 0.034 inch, and a distal portion length DL of 0.007 inch. Headpiece 104a defines a headpiece lumen 122a, shown in phantom, having a diameter of approximately 0.004 inch and extending from distal end 107a to proximal end 150a. A ring 106a has a longitudinal length RL of 0.001 and an overall diameter of 0.015 inch. Ring 106a separates proximal portion 102a, having a mean proximal diameter of 0.008 inch, from distal portion 152a, having a mean distal diameter of 0.009. In other constructions, the mean proximal and distal diameters are substantially the same, as shown in FIG. 4, or may differ by a larger amount, depending on the expected lumen diameters of a delivery catheter gripper portion and a proximal coil lumen, respectively, to be matched with the different portions of the headpiece. Preferably, proximal end 150a, FIG. 6, is curved or chamfered to facilitate mating with the delivery catheter gripper portion, and headpiece 104a is formed of substantially the same material as the helically wound coil to which it will be attached by a secure bond as described above.

Anchor filament 120a, FIG. 7, is formed in this construction using round platinum-tungsten alloy wire, preferably substantially the same alloy as utilized for the headpiece and helically wound coil, having a diameter of approximately 0.0015 inch, and a length more than twice as great as the combined length of the helically wound coil with attached proximal headpiece. The alloy wire is bent approximately in half, that is, it is doubled over, to form a wire loop having a bight 124a defining an eye 126a with two wire legs 116a and 118a extending in parallel from the bight 124a such as shown in FIG. 7, with an effective length that is greater than the total combined length of the coil and headpiece. The coil with attached headpiece is placed in a first, anchor filament advancement fixture to apply force to both ends until the longitudinal axis becomes substantially non-curved. The anchor bight is advanced distally, through the headpiece lumen and central coil lumen, by pushing on ends 160a and 162a or by grasping the wire legs 116a and 118a of anchor filament 120a, until the bight 124a emerges beyond the distal end of the helically wound coil. After the anchor bight 124a is exposed, a stretch resistant member is threaded through the eye to form a loop extending distally away from the coil.

Sutures provide acceptable stretch resistant members. A preferred non-absorbable suture is PROLENE® polypropylene monofilament suture, especially size 10-0 which is thinner than a human hair, available from Ethicon, Inc. Preferred absorbable sutures include VICRYL® polyglycolic acid monofilament or multifilament sutures, also available from Ethicon, Inc. Other polymeric or metallic fibres or wires can be utilized as desired according to the present invention. Further, the material utilized for the stretch resistant member, or an additive to that material, may be selected to have thrombogenic properties to promote clotting.

Next, the anchor filament with joined stretch resistant member is pulled proximally until the bight is positioned to be spaced several coil wire diameters from the distal end of the headpiece such as shown in FIG. 4. This bight alignment step can be accomplished at the first, anchor filament advancement fixture to maintain a substantially linear longitudinal coil axis, or at another fixture at a subsequent manufacturing station to straighten the helically wound coil during this step. Proper alignment is determined visually in one procedure according to the present invention by counting between one to six coil turns extending distally from the headpiece, and positioning the bight within that range of coil turns. It is preferred that the bight does not contact any edges of the headpiece, thereby avoiding potential chafing against the bight or the stretch resistant member. One advantage of the present invention is that axial adjustment of the bight during this step of manufacture is readily accomplished by pulling the anchor filament proximally or pulling the stretch resistant member distally to change the position of the bight relative to the headpiece.

After the bight is properly positioned relative to the distal end of the headpiece, excess anchor filament material is trimmed. Heat, such as a plasma flame if the anchor filament is metallic, is applied to the remaining proximal filament ends until they melt and a proximal bead is formed at the proximal end of the headpiece, extending into the headpiece lumen such as shown in FIG. 4, to secure the anchor filament to the headpiece with structural integrity as soon as the bead solidifies. Preferably, the proximal bead appears flush with or smaller than the outer diameter of the headpiece. The solidified proximal bead also restores hydraulic integrity to the headpiece by sealing the headpiece lumen.

Excess stretch resistant member material extending beyond the distal end of the coil is then trimmed, and heat is applied to melt the ends of the remaining material to form a distal bead, preferably concentric and substantially hemispherical in shape with a substantially smooth, atraumatic, low-friction outer surface to facilitate entry and conformance of the occlusive device during its delivery into a malformation of a patient. The amount of stretching of the helically wound coil permitted by the stretch resistant member depends on factors including the composition and thickness of stretch resistant member material, including its tensile properties, as well as the overall length of the stretch resistant member. For example, any desired amount of slack relative to the length of the coil can be established during manufacture by elongating the coil by the desired amount using a fixture before melting the distal portion of the stretch resistant member to form the distal bead, which generates that amount of slack in the stretch resistant member when the coil is released from the fixture.

The anchor filament and stretch resistant member together form a stretch-resistant assembly extending through the coil lumen and the headpiece lumen to minimize coil elongation when pulling forces are applied to the occlusive device. It is desirable for the stretch-resistant assembly to have a pull strength of at least 0.02 pounds at its proximal and distal ends when the pull strength of the coil to headpiece solder joint is about 0.05 pounds.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A stretch-resistant occlusive device comprising:
    a helically wound coil defining a coil lumen extending along the entire axial length of the coil, the coil having a proximal end portion and a distal end portion;
    a headpiece having a proximal end and a distal end, the distal end being attached to the proximal end portion of the coil, and defining a headpiece lumen extending between the proximal and distal ends of the headpiece;
    an anchor filament extending through the headpiece lumen, having at least one proximal end secured to the proximal end of the headpiece, and having a distal portion defining an eye positioned distal to the distal end of the headpiece, the anchor filament being a single continuous element that is folded at the distal end to form the eye; and
    a stretch resistant member, positioned within the coil lumen, having a proximal portion extending through the eye and having at least one distal end secured to the distal end of the coil;
    wherein the helically wound coil is substantial cylindrical and defines the coil lumen to have a lumen diameter at its proximal end; and wherein the headpiece is substantially cylindrical with a mean distal diameter and a mean proximal diameter, and further includes at least one stop element positioned between the proximal and distal mean diameters and projecting radially outwardly beyond both mean diameters.

2. The occlusive device of claim 1 wherein the anchor filament has two proximal ends secured to the proximal end of the headpiece with structural and hydraulic integrity, and has a distal bight portion defining the eye.

3. The occlusive device of claim 1 wherein the stretch resistant member has two distal ends secured to the distal end of the coil.

4. The occlusive device of claim 1 wherein the anchor filament and the stretch resistant member are composed of different materials.

5. The occlusive device of claim 1 wherein the anchor filament includes metallic material and the stretch resistant member includes a loop of polymeric material.

6. The occlusive device of claim 5 wherein the anchor filament and the headpiece are composed of substantially the same material.

7. The occlusive device of claim 1 wherein the anchor filament, the headpiece and the helically wound coil are all composed of substantially the same material.

8. The occlusive device of claim 1 wherein the stop element includes a ring member having a stop diameter that is greater than the mean diameters of the headpiece and is greater than the proximal coil lumen diameter.

9. The occlusive device of claim 1, wherein the anchor filament is a continuous wire.

10. A stretch-resistant embolic coil comprising:
- a substantially cylindrical helically wound coil defining a coil lumen extending along the entire axial length of the coil, the coil having a distal end portion and a proximal end portion with a proximal coil lumen diameter;
- a substantially cylindrical headpiece having an elongated proximal end with a mean proximal diameter, having a distal end with a mean distal diameter attached to the proximal end portion of the coil, having at least one stop element positioned between the proximal and distal mean diameters, and defining a headpiece lumen extending between the proximal and distal ends of the headpiece;
- an anchor filament extending through the headpiece lumen, having two proximal ends secured to the proximal end of the headpiece with structural and hydraulic integrity, and having a distal bight portion defining an eye positioned distal to the distal end of the headpiece, the anchor filament being a single continuous element that is folded at the distal end to form the eye; and
- a stretch resistant member, positioned within the coil lumen, having a proximal portion extending through the eye and having two distal ends secured to the distal end of the coil.

11. The embolic coil of claim 10 wherein the stop element includes a ring member having a stop diameter that is greater than the mean diameters of the headpiece and is greater than the proximal coil lumen diameter.

12. The embolic coil of claim 10 wherein the anchor filament is composed of metallic material.

13. The occlusive device of claim 12 wherein the anchor filament and the headpiece are composed of substantially the same material.

14. The occlusive device of claim 10 wherein the anchor filament, the headpiece and the helically wound coil are all composed of substantially the same material.

15. The embolic coil of claim 10 wherein the stretch resistant member is composed of polymeric material.

16. The embolic coil of claim 10, wherein the anchor filament is a continuous wire.

* * * * *